US008041463B2

(12) United States Patent
Pollack et al.

(10) Patent No.: US 8,041,463 B2
(45) Date of Patent: Oct. 18, 2011

(54) MODULAR DROPLET ACTUATOR DRIVE

(75) Inventors: Michael G. Pollack, Durham, NC (US);
Philip Paik, Chula Vista, CA (US)

(73) Assignees: Advanced Liquid Logic, Inc., Research Triangle Park, NC (US); Duke University, Durham, NC (US)

(*) Notice: Subject to any disclaimer, the term of this patent is extended or adjusted under 35 U.S.C. 154(b) by 0 days.

(21) Appl. No.: 12/707,081

(22) Filed: Feb. 17, 2010

(65) Prior Publication Data
US 2010/0143963 A1      Jun. 10, 2010

Related U.S. Application Data

(63) Continuation of application No. PCT/US2008/073673, filed on Aug. 20, 2008, and a continuation-in-part of application No. 11/838,388, filed on Aug. 14, 2007, now Pat. No. 7,822,510, which is a continuation of application No. PCT/US2007/011298, filed on May 9, 2007.

(60) Provisional application No. 60/746,797, filed on May 9, 2006, provisional application No. 60/806,412, filed on Jun. 30, 2006, provisional application No. 60/956,774, filed on Aug. 20, 2007, provisional application No. 60/980,503, filed on Oct. 17, 2007.

(51) Int. Cl.
*G05D 7/00* (2006.01)
*G05D 11/00* (2006.01)
*G01N 7/00* (2006.01)
*B05C 11/00* (2006.01)

(52) U.S. Cl. ........ 700/283; 700/282; 73/64.52; 118/712

(58) Field of Classification Search ................. 700/283, 700/282; 118/712; 73/64.52; 164/19
See application file for complete search history.

(56) References Cited

U.S. PATENT DOCUMENTS

| 4,390,403 | A | | 6/1983 | Batchelder |
| 4,863,849 | A | | 9/1989 | Melamede |
| 5,486,337 | A | | 1/1996 | Ohkawa |
| 5,644,239 | A | * | 7/1997 | Huang et al. ............ 324/439 |
| 5,721,851 | A | | 2/1998 | Cline et al. |
| 5,770,391 | A | | 6/1998 | Foote et al. |

(Continued)

FOREIGN PATENT DOCUMENTS

WO      WO9822625 A1      5/1998
(Continued)

OTHER PUBLICATIONS

T. Taniguchi et al., "Chemical reactions in microdroplets by electrostatic manipulation of droplets in liquid media," Lab on a Chip, vol. 2, No. 2, pp. 19-23 (2002).

(Continued)

*Primary Examiner* — Ramesh Patel
(74) *Attorney, Agent, or Firm* — William A. Barrett; Ward and Smith, P.A.

(57) ABSTRACT

A droplet actuator drive including a detection apparatus for sensing a property of a droplet on a droplet actuator; circuitry for controlling the detection apparatus electronically coupled to the detection apparatus; a droplet actuator cartridge connector arranged so that when a droplet actuator cartridge electronically is coupled thereto: the droplet actuator cartridge is aligned with the detection apparatus; and the detection apparatus can sense the property of the droplet on a droplet actuator; circuitry for controlling a droplet actuator coupled to the droplet actuator connector; and the droplet actuator circuitry may be coupled to a processor.

15 Claims, 5 Drawing Sheets

U.S. PATENT DOCUMENTS

| | | | |
|---|---|---|---|
| 5,846,396 A * | 12/1998 | Zanzucchi et al. | 506/33 |
| 5,851,769 A | 12/1998 | Gray et al. | |
| 5,980,719 A | 11/1999 | Cherukuri et al. | |
| 6,106,685 A | 8/2000 | McBride et al. | |
| 6,210,891 B1 | 4/2001 | Nyren et al. | |
| 6,221,226 B1 * | 4/2001 | Kopf-Sill | 204/602 |
| 6,258,568 B1 | 7/2001 | Nyren | |
| 6,294,063 B1 * | 9/2001 | Becker et al. | 204/450 |
| 6,319,668 B1 | 11/2001 | Nova et al. | |
| 6,379,929 B1 | 4/2002 | Burns et al. | |
| 6,432,290 B1 | 8/2002 | Harrison et al. | |
| 6,452,609 B1 * | 9/2002 | Katinsky et al. | 715/716 |
| 6,473,492 B2 | 10/2002 | Prins | |
| 6,485,913 B1 | 11/2002 | Becker et al. | |
| 6,538,823 B2 | 3/2003 | Kroupenkine et al. | |
| 6,545,815 B2 | 4/2003 | Kroupenkine et al. | |
| 6,565,727 B1 | 5/2003 | Shenderov | |
| 6,629,826 B2 | 10/2003 | Yoon et al. | |
| 6,665,127 B2 | 12/2003 | Bao et al. | |
| 6,761,962 B2 | 7/2004 | Bentsen et al. | |
| 6,773,566 B2 | 8/2004 | Shenderov | |
| 6,828,100 B1 | 12/2004 | Ronaghi | |
| 6,841,128 B2 | 1/2005 | Kambara et al. | |
| 6,896,855 B1 | 5/2005 | Kohler et al. | |
| 6,911,132 B2 | 6/2005 | Pamula et al. | |
| 6,949,176 B2 | 9/2005 | Vacca et al. | |
| 6,958,132 B2 | 10/2005 | Chiou et al. | |
| 6,960,437 B2 | 11/2005 | Enzelberger et al. | |
| 6,989,234 B2 | 1/2006 | Kolar et al. | |
| 7,078,168 B2 | 7/2006 | Sylvan | |
| 7,163,612 B2 * | 1/2007 | Sterling et al. | 204/600 |
| 7,189,359 B2 | 3/2007 | Yuan et al. | |
| 7,189,560 B2 | 3/2007 | Kim et al. | |
| 7,215,425 B2 | 5/2007 | Rezachek et al. | |
| 7,693,666 B2 | 4/2010 | Griffith et al. | |
| 2002/0043463 A1 | 4/2002 | Shenderov | |
| 2002/0055167 A1 | 5/2002 | Pourahmadi et al. | |
| 2002/0058332 A1 | 5/2002 | Quake et al. | |
| 2002/0093651 A1 | 7/2002 | Roe | |
| 2002/0128546 A1 | 9/2002 | Silver | |
| 2002/0142471 A1 | 10/2002 | Handique et al. | |
| 2002/0168671 A1 | 11/2002 | Burns et al. | |
| 2002/0172969 A1 | 11/2002 | Burns et al. | |
| 2003/0006140 A1 | 1/2003 | Vacca et al. | |
| 2003/0012483 A1 | 1/2003 | Ticknor et al. | |
| 2003/0012699 A1 | 1/2003 | Moore et al. | |
| 2003/0082081 A1 | 5/2003 | Fouillet et al. | |
| 2003/0103021 A1 | 6/2003 | Young et al. | |
| 2003/0119057 A1 | 6/2003 | Gascoyne et al. | |
| 2003/0164295 A1 | 9/2003 | Sterling | |
| 2003/0183525 A1 | 10/2003 | Elrod et al. | |
| 2003/0205632 A1 | 11/2003 | Kim et al. | |
| 2003/0206351 A1 | 11/2003 | Kroupenkine | |
| 2003/0224528 A1 | 12/2003 | Chiou et al. | |
| 2003/0227100 A1 | 12/2003 | Chandross et al. | |
| 2004/0007377 A1 | 1/2004 | Fouillet et al. | |
| 2004/0031688 A1 | 2/2004 | Shenderov | |
| 2004/0042721 A1 | 3/2004 | Kroupenkine et al. | |
| 2004/0055536 A1 | 3/2004 | Kolar et al. | |
| 2004/0055891 A1 | 3/2004 | Pamula et al. | |
| 2004/0058450 A1 | 3/2004 | Pamula et al. | |
| 2004/0091392 A1 | 5/2004 | McBridge et al. | |
| 2004/0136876 A1 | 7/2004 | Fouillet et al. | |
| 2004/0141884 A1 | 7/2004 | Unno et al. | |
| 2004/0231987 A1 * | 11/2004 | Sterling et al. | 204/450 |
| 2004/0260429 A1 * | 12/2004 | Saelens | 700/283 |
| 2005/0048581 A1 | 3/2005 | Chiu et al. | |
| 2005/0056569 A1 * | 3/2005 | Yuan et al. | 209/215 |
| 2005/0064423 A1 | 3/2005 | Higuchi et al. | |
| 2005/0100675 A1 | 5/2005 | Mao et al. | |
| 2005/0120030 A1 | 6/2005 | Varpela et al. | |
| 2005/0136551 A1 | 6/2005 | Mpock | |
| 2005/0148042 A1 | 7/2005 | Prestwich et al. | |
| 2005/0158755 A1 | 7/2005 | Lee et al. | |
| 2005/0179746 A1 | 8/2005 | Roux et al. | |
| 2005/0227264 A1 | 10/2005 | Nobile et al. | |
| 2005/0287572 A1 | 12/2005 | Mathies et al. | |
| 2006/0009705 A1 | 1/2006 | Brown | |
| 2006/0021875 A1 | 2/2006 | Griffith et al. | |
| 2006/0054503 A1 | 3/2006 | Pamula et al. | |
| 2006/0068450 A1 | 3/2006 | Combette et al. | |
| 2006/0078935 A1 | 4/2006 | Werner et al. | |
| 2006/0166261 A1 | 7/2006 | Higuchi et al. | |
| 2006/0166262 A1 | 7/2006 | Higuchi et al. | |
| 2006/0172336 A1 | 8/2006 | Higuchi et al. | |
| 2006/0254933 A1 | 11/2006 | Adachi et al. | |
| 2007/0141593 A1 | 6/2007 | Lee et al. | |
| 2008/0138815 A1 | 6/2008 | Brown et al. | |
| 2008/0153091 A1 | 6/2008 | Brown et al. | |
| 2008/0160525 A1 | 7/2008 | Brown et al. | |
| 2008/0169184 A1 | 7/2008 | Brown et al. | |
| 2008/0171324 A1 | 7/2008 | Brown et al. | |
| 2008/0171325 A1 | 7/2008 | Brown et al. | |
| 2008/0171326 A1 | 7/2008 | Brown et al. | |
| 2008/0171327 A1 | 7/2008 | Brown et al. | |
| 2008/0171382 A1 | 7/2008 | Brown et al. | |
| 2008/0213766 A1 | 9/2008 | Brown et al. | |
| 2008/0281471 A1 * | 11/2008 | Smith et al. | 700/266 |
| 2009/0042319 A1 | 2/2009 | De Guzman et al. | |
| 2009/0253130 A1 | 10/2009 | Yoo | |

FOREIGN PATENT DOCUMENTS

| | | |
|---|---|---|
| WO | WO9915876 A1 | 4/1999 |
| WO | WO9917093 A1 | 4/1999 |
| WO | WO9954730 A1 | 10/1999 |
| WO | WO03069380 A1 | 8/2003 |
| WO | WO2004027490 A1 | 4/2004 |
| WO | WO2006026351 A1 | 3/2006 |
| WO | WO2007073107 A1 | 6/2007 |
| WO | WO2007133710 A2 | 11/2007 |

OTHER PUBLICATIONS

Dewey A, Srinivasan V, Icoz E, "Visual modeling and design of microelectromechanical system transducers", Microelectronics Journal, vol. 32, pp. 373-381, Apr. 2001.

Dewey A, Srinivasan V, Icoz E, "Towards a visual modeling approach to designing micro electromechanical system transducers," Journal of Micromechanics and Microengineering, vol. 9, pp. 332-340, Dec. 1999.

R.B. Fair, A. Khlystov, T. Tailor, V. Ivanov, R.D. Evans, V. Srinivasan, V. Pamula, M.G. Pollack, P.B. Griffin, and J. Zhoud, "Chemical and Biological Applications of Digital Microfluidic Devices", IEEE Design and Test of Computers, vol. 24(1): pp. 10-24 Jan.-Feb. 2007.

R.B. Fair, A. Khlystov, V. Srinivasan, V. K. Pamula, K.N. Weaver, "Integrated chemical/biochemical sample collection, pre-concentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.

R.B. Fair, V. Srinivasan, V.K. Pamula, and K.N. Weaver, "Bead-Based and Solution-Based Assays Performed on a Digital Microfluidic Platform," Biomedical Engineering Society (BMES) Fall Meeting, Baltimore, MD, Oct. 1, 2005.

R.B. Fair, V. Srinivasan, H. Ren, P. Paik, V.K. Pamula, M.G. Pollack, "Electrowetting-based On-Chip Sample Processing for Integrated Microfluidics," IEEE Inter. Electron Devices Meeting (IEDM), pp. 32.5.1-32.5.4, 2003.

Phil Paik, Vamsee K. Pamula, and K. Chakrabarty, "Thermal effects on Droplet Transport in Digital Microfluidics with Applications to Chip Cooling Processing for Integrated Microfluidics," International Conference on Thermal, Mechanics, and Thermomechanical Phenomena in Electronic Systems (ITherm), pp. 649-654, 2004.

Phil Paik, Vamsee K. Pamula, and Richard B. Fair, "Rapid droplet mixers for digital microfluidic systems," Lab on a Chip, vol. 3, pp. 253-259, 2003.

Phil Paik, Vamsee K. Pamula, Michael G. Pollack and Richard B. Fair, "Electrowetting-based droplet mixers for microfluidic systems", Lab on a Chip (LOC), vol. 3, pp. 28-33, 2003.

Vamsee K. Pamula and Krishnendu Chakrabarty, "Cooling of integrated circuits using droplet-based microfluidics," Proc. ACM Great Lakes Symposium on VLSI, pp. 84-87, Apr. 2003.

V.K. Pamula, V. Srinivasan, H. Chakrapani, R.B. Fair, E.J. Toone, "A droplet-based lab-on-a-chip for colorimetric detection of nitroaromatic explosives," Proceedings of Micro Electro Mechanical Systems, pp. 722-725, 2005.

M. G. Pollack, P. Y. Paik, A. D. Shenderov, V. K. Pamula, F. S. Dietrich, and R. B. Fair, "Investigation of electrowetting-based microfluidics for real-time PCR applications," µTAS 2003.

Pollack et al., "Electrowetting-Based Microfluidics for High-Throughput Screening," smallTalk2001 Conference Program Abstract (Aug. 2001), p. 149, San Diego.

Hong Ren, Vijay Srinivasan, Michael G. Pollack, and Richard B. Fair, "Automated electrowetting-based droplet dispensing with good reproducibility," Proc. Micro Total Analysis Systems (mTAS), pp. 993-996, 2003.

Hong Ren, Vijay Srinivasan, and Richard B. Fair, "Design and testing of an interpolating mixing architecture for electrowetting-based droplet-on-chip chemical dilution", Transducers 2003, pp. 619-622, 2003.

Vijay Srinivasan, Vamsee K. Pamula, Richard B. Fair, "An integrated digital microfluidic lab-on-a-chip for clinical diagnostics on human physiological fluids," Lab on a Chip, vol. 4, pp. 310-315, 2004.

Vijay Srinivasan, Vamsee K. Pamula, Richard B. Fair, "Droplet-based microfluidic lab-on-a-chip for glucose detection," Analytica Chimica Acta, vol. 507, No. 1, pp. 145-150, 2004.

V. Srinivasan, V.K. Pamula, P. Paik, and R.B. Fair, "Protein Stamping for MALDI Mass Spectrometry Using an Electrowetting-based Microfluidic Platform," Lab-on-a-Chip: Platforms, Devices, and Applications, Conf. 5591, SPIE Optics East, Philadelphia, Oct. 25-28, 2004.

Vijay Srinivasan, Vamsee K. Pamula, Michael G. Pollack, and Richard B. Fair, "Clinical diagnostics on human whole blood, plasma, serum, urine, saliva, sweat, and tears on a digital microfluidic platform," Proc. Micro Total Analysis Systems (mTAS), pp. 1287-1290, 2003.

Vijay Srinivasan, Vamsee K. Pamula, Michael G. Pollack, and Richard B. Fair, "A digital microfluidic biosensor for multianalyte detection", Proc. IEEE 16th Micro Electro Mechanical Systems Conference, pp. 327-330, 2003.

Vijay Srinivasan, Vamsee K. Pamula, K. Divakar Rao, Michael G. Pollack, Joseph A. Izatt, and Richard B. Fair, "3-D imaging of moving droplets for microfluidics using optical coherence tomography," Proc. Micro Total Analysis Systems (mTAS), pp. 1303-1306, 2003.

F. Su, S. Ozev and K. Chakrabarty, "Testing of droplet-based microelectrofluidic systems", Proc. IEEE International Test Conference, pp. 1192-1200, 2003.

Nicole Weaver, "Application of Magnetic Microspheres for Pyrosequencing on a Digital Microfluidic Platform", Aug. 2005.

PCT International Preliminary Report on Patentability for PCT/US2005/030247 dated Feb. 28, 2007.

PCT International Search Report and Written Opinion for PCT/US2006/047486 dated May 2, 2008.

PCT International Search Report and Written Opinion for PCT/US2006/047481 dated May 5, 2008.

PCT International Search Report and Written Opinion for PCT/US2007/011298 dated Jun. 25, 2008.

PCT International Search Report and Written Opinion for PCT/US2007/009379 dated Aug. 18, 2008.

"Chip mixes droplets faster", MIT Technology Review, Oct. 2003.

"Chip Juggles Droplets", Technology Research News, Sep. 4-11, 2002.

"Laboratory on a Chip", Popular Mechanics, Mar. 2002.

"Lab-on-a-Chip Technology May Present New ESD Challenges", Electrostatic Discharge Journal, Mar. 2002.

"Making materials fit the future: accommodating relentless technological requirements means researchers must recreated and reconfigure materials, frequently challenging established laws of physics, while keeping an eye on Moore's law", R&D Magazine, Dec. 2001.

Vijay Srinivasan, Anand Jog and Richard B. Fair, "Scalable Macromodels for Microelectromechanical Systems", Technical Proc. 2001 Int. Conf. on Modeling and Simulation of Microsystems, pp. 72-75, 2004.

Ali Agah, "DNA Analysis Chip by Electrowetting Actuation," Stanford Nanofabrication Facility, p. 9, 2002.

Bhansali et al- "Resolving chemical/bio-compatibility issues in microfluidic MEMS systems," SPIE Conference on Microfluidic Devices and Systems II, vol. 3877, Santa Clara, CA, pp. 101-109 (1999).

Cho et al., "Concentration and binary separation of micro particles for droplet-based digital microfluidics," Lab Chip, vol. 7, pp. 490-498, 2007.

Lehmann et al., "Droplet-Based DNA Purification in a Magnetic Lab-on-a-Chip," Angewandte Chemie, vol. 45, pp. 3062-3067, 2006.

N. Pamme, "Magnetism and microfluidics," Lab on a Chip (LOC), vol. 6, pp. 24-38, 2006.

Juergen Pipper et al., "Clockwork PCR Including Sample Preparation," Angew. Chem. Int. Ed., vol. 47, pp. 3900-3904, 2008.

Olivier Raccurt et al., "On the influence of surfactants in electrowetting systems," J. Micromech. Microeng., vol. 17, pp. 2217-2223 (2007).

Jean-Maxime Roux and Yves Fouillet, "3D droplet displacement in microfluidic systems by electrostatic actuation," Sensors and Actuators A, vol. 134, Issue 2, pp. 486-493, Mar. 15, 2007.

R. Sista, "Development of a Digital Microfluidic Lab-on-a-Chip for Automated Immunoassay with Magnetically Responsive Beads", PhD Thesis, Department of Chemical Engineering, Florida State University, 2007.

E. Verpoorte, "Beads and chips: new recipes for analysis," Lab on a Chip (LOC), vol. 3, pp. 60N-68N, 2003.

Y. Wang et al., "Effcient in-droplet separation of magnetic particles for digital microfluidics," Journal of Micromechanics and Microengineering, vol. 17, pp. 2148-2156 (2007).

Masao Washizu, "Electrostatic Actuation of Liquid Droplets for Micro-Reactor Applications", IEEE Industry Applications Society Annual Meeting, pp. 1867-1873, Oct. 5-9, 1997.

Wheeler et al., "Electrowetting-on-dielectric for analysis of peptides and proteins by matrix assisted laser desorption/ionization mass spectrometry," Solid-State Sensor, Actuator and Microsystems Workshop publication, pp. 402-403, Jun. 6-10, 2004.

Aaron R. Wheeler, "Putting Electrowetting to Work," Science, vol. 322, No. 5901, pp. 539-540, Oct. 24, 2008.

Yi et al., "Geometric surface modification of nozzles for complete transfer of liquid drops," Solid-State Sensor, Actuator and Microsystems Workshop, pp. 164-167, Jun. 6-10, 2004.

T.H. Zhang, K. Chakrabarty, R.B. Fair, "Behavioral modeling and performance evaluation of microelectrofluidics-based PCR systems using SystemC", IEEE Transactions on Computer-Aided Design of Integrated Circuits & Systems, vol. 23 (6): pp. 843-858, Jun. 2004.

"Agilent 2100 Bioanalyzer 2100 Expert User's Guide", Nov. 2003, Agilent Technologies, pp. 23, 47, 56, 57, and 398.

Jian Gong et al., "Portable digital microfluidics platform with active but disposable Lab-On-Chip," Micro Electro Mechanical Systems, 17th IEEE International Conference on (MEMS), Maastricht, Netherlands, Jan. 25-29, 2004; Piscataway, NJ, IEEE, Jan. 25, 2004, pp. 355-358.

Pollack et al., "Electrowetting-Based Actuation of Droplets for Integrated Microfluidics," Lab on a Chip (LOC), vol. 2, pp. 96-101, 2002.

H. Ren, and R. B. Fair "Micro/Nano Liter Droplet Formation and Dispensing by Capacitance Metering and Electrowetting Actuation", IEEE-NANO 2002, pp. 369-372, 2002.

Altti Torkkeli, "Droplet microfluidics on a planar surface," Doctoral Dissertation, Department of Electrical Engineering, Helsinki University of Technology (Oct. 3, 2003).

PCT International Search Report and Written Opinion for PCT/US2007/011298 dated Jun. 25, 2008.

PCT International Search Report and Written Opinion for PCT/US2008/073673 dated Mar. 13, 2009.

Jie Ding, "System level architectural optimization of semi-reconfigurable microfluidic system," M.S. Thesis, Duke University Dept of Electrical Engineering, 2000.

Moon, Hyejin, Ph.D., "Electrowetting-on-dielectric microfluidics: Modeling, physics, and MALDI application," University of California, Los Angeles, 2005.

Terry, S.C., J.H. Jerman, and J.B. Angell, "A Gas Chromatographic Air Analyzer Fabricated on a Silicon Wafer," IEEE Transactions on Electron Devices, vol. ED-26, 1979, pp. 1880-1886.

Tuckerman, D.B. and R.F.W. Pease, "High-Performance Heat Sinking for VLSI," IEEE Electron Device Letters, 1981, pp. 126-129.

Batchelder, J.S., " Dielectrophoretic manipulator," Review of Scientific Instruments, vol. 54, 1983, pp. 300-302.

Manz, A., N. Graber, and H.M. Widmer, "Miniaturized Total Chemical Analysis Systems: a Novel Concept for Chemical Sensing," Sensors and Actuators B: Chemical, 1990, pp. 244-248.

Welters, W.J.J. and L.G.J. Fokkink, "Fast Electrically Switchable Capillary Effects," Langmuir, vol. 14, Mar. 1998, pp. 1535-1538.

McDonald, J.C., D.C. Duffy, J.R. Anderson, D.T. Chiu, H. Wu, O.J.A. Schuueller, and G.M. Whitesides, "Fabrication of Microfluidic systems in poly (dimethylsiloxane)," Electrophoresis, vol. 21, 2000, pp. 27-40.

A. Wego, S. Richter, L. Pagel, "Fluidic microsystems based on printed circuit board technology," Journal of Micromechanics and Microengineering, vol. 11, No. 5, pp. 528-531 (Sep. 2001).

Moon H, Cho SK, Garrell RL, et al., "Low voltage electrowetting-on-dielectric," Journal of Applied Physics, vol. 92 (7): pp. 4080-4087, Oct. 1, 2002.

Locascio, L.E., et al. "Polymer microfluidic devices," Talanta, vol. 56, Feb. 2002, pp. 267-287.

Garrell, R.L. et al., "Preventing Biomolecular Adsorption in Electrowetting-Based Biofluidic Chips," Analytical Chemistry, vol. 75, Oct. 2003, pp. 5097-5102.

P.Y. Chiou, H. Moon, H. Toshiyoshi, C.-J. Kim, and M.C. Wu, "Light actuation of liquid by optoelectrowetting," Sensors and Actuators A: Physical, vol. 104, May 2003, pp. 222-228.

Squires, T.M. and S.R. Quake, "Microfluidics: Fluid physics at the nanoliter scale," Reviews of Modern Physics, vol. 77, Oct. 2005, pp. 977-1-26.

Fouillet, Y., D. Jary, A.G. Brachet, C. Chabrol, J. Boutet, P. Clementz, R. Charles, and C. Peponnet, "Design and Validation of a Complex Generic Fluidic Microprocessor Based on EWOD Droplet for Biological Applications," 9th International Conference on Miniaturized Systems for Chemistry and Life Sciences (MicroTAS), Boston, MA: 2005, pp. 58-60.

Z. Guttenberg, H. Muller, H. Habermuller, A. Geisbauer, J. Pipper, J. Felbel, M. Kielpinski, J. Scriba, and A. Wixforth, "Planar chip devices for PCR and hybridization with surface acoustic wave pump.," Lab on a chip, vol. 5, Mar. 2005, pp. 12617-12622.

Yager, P., T. Edwards, E. Fu, K. Helton, K. Nelson, M.R. Tam, and B.H. Weigl, "Microfluidic diagnostic technologies for global public health," Nature, vol. 442, 2006, pp. 412-418.

Cooney, C.G., C-Y. Chen, M.R. Emerling, A Nadim, and J.D. Sterling, Microfluidics and Nanofluidics, vol. 2 Mar. 2006, pp. 435-446.

Chatterjee, D., B. Hetayothin, A.R. Wheeler, D.J. King, and R.L. Garrell, "Droplet-based microfluidics with nonaqueous solvents and solutions.," Lab on a Chip, vol. 6, Feb. 2006, pp. 199-206.

M.Madou, J. Zoval, G. Jia, H. Kido, J. Kim, "Lab on a CD," Annual Review of Biomedical Engineering, vol. 8, pp. 601-628, 2006.

Yi, U.-C. and C.-J. Kim, "Characterization of electrowetting actuation on addressable single-side coplanar electrodes," Journal of Micromechanics and Microengineering, vol. 16, Oct. 2006, pp. 2053-2059.

Dubois, P., G. Marchand, Y. Fouillet, J. Berthier, T. Douki, F. Hassine, S. Gmouh, and M. Vaultier, "Ionic Liquid Droplet as e-Microreactor," Analytical Chemistry, vol. 78, 2006, pp. 4909-4917.

Whitesides, G.M., "The origins and the future of microfluidics," Nature, vol. 442, 2006, pp. 368-373.

Chin, C.D., V. Linder, and S.K. Sia, "Lab-on-a-chip devices for global health: past studies and future opportunities.," Lab on a Chip, vol. 7, Jan. 2007, pp. 41-57.

Baviere, R., J. Boutet, and Y. Fouillet, "Dynamics of droplet transport induced by electrowetting actuation," Microfluidics and Nanofluidics, vol. 4, May 2007, pp. 287-294.

Paik, P.Y. ,V.K. Pamula, and K. Chakrabarty, "A Digital-Microfluidic Approach to Chip Cooling," IEEE Design & Test of Computers, vol. 25, Jul. 2008, pp. 372-381.

The, S. -Y., R. Lin, L.-H. Hung, and A.P. Lee, "Droplet microfluidics.," Lab on a chip, vol. 8 Feb. 2008, pp. 198-220.

I.Barbulovic-Nad, H. Yang, P.S. Park, and A.R. Wheeler, "Digital microfluidics for cell-based assays.," Lab ona chip, vol. 8, Apr. 2008, pp. 519-526.

Huebner, A., S. Sharma, M. Srisa-Art, F. Hollfelder, J.B. Edel, and A.J. DeMello, "Microdroplets: a sea of applications?," Lab on a Chip, vol. 8, Aug. 2008, pp. 1244-1254.

Gong, J. and C.-J.C. Kim, "Direct-referencing two-dimensional-array digital microfluidics using multi-layer printed circuit board," Journal of Microelectromechanical Systems, vol. 17, Jan. 2008, pp. 257-264.

Miller, E.M. and A.R. Wheeler, "A Digital Microfluidic Approach to Homogeneous Enzyme Assays," Analytical Chemistry, vol. 80, 2008, pp. 1614-1619.

R.S. Sista, A.E. Eckhardt, V. Srinivasan, M.G. Pollack, S. Palanki, and V.K. Pamula, "Heterogeneous immunoassays using magnetic beads on a digital microfluidic platform," Lab on a Chip, vol. 8, Dec. 2008, pp. 2188-2196.

R. Sista, Z. Hua, P. Thwar, A Sudarsan, V. Srinivasan, A Eckhardt, M. Pollack, and V. Pamula, "Development of a digital microfluidic platform for point of care testing.," Lab on a chip, vol. 8, Dec. 2008, pp. 2091-2104.

Luk, V.N., Pluronic additives: a solution to sticky problems in digital microfluidics.,: Langmuir: the ACS journal of surfaces ans colloids, vol. 24, Jun. 2008, pp. 6382-6389.

L. Luan, R.D. Evans, N.M. Jokerst, and R.B. Fair, "Integrated Optical Sensor in a Digital Microfluidic Platform," IEEE Sensors Journal, vol. 8, May 2008, pp. 628-635.

R. Mariella, "Sample preparation: the weak link in microfluidics-based biodetection.," Biomedical Microdevices, vol. 10, Dec. 2008, pp. 777-784.

D. Brassard, L. Malic, F. Normandin, M. Tabrizian, and T. Veres, "Water-oil core-shell droplets for electrowetting-based digital microfluidic devices.," Lab on a chip, vol. 8, Aug. 2008, pp. 1342-1349.

R. Mukhopadhyay, "Microfluidics: on the slope of enlightenment.," Analytical chemsitry vol. 81, Jun. 2009, pp. 4169-4173.

N.A. Mousa, M.J. Jebrail, H.Yang, M. Abdelgawad, P. Metalnikov, J. Chen, A.R. Wheeler, and R.F. Casper, "Droplet-scale estrogen assays in breast tissue, blood, and serum.," Science Translational Medicine, vol. 1 Oct. 2009, p. Ira2.

J.L. Poulos, W.C. Nelson, T.-J. Jeon, C.-J. "CJ" Kim, and J.J. Schmidt, "Electrowetting on dielectric-based microfluidics for integrated lipid bilayer formation and measurement," Applied Physics Letters, vol. 95, 2009, p. 013706.

S.M. Langelier, D.S. Chang, R.I. Zeitoun, and M. a Burns, "Acoustically driven programmable liquid motion using resonance cavities" Proceedings of the National Academy of Sciences of the USA, vol. 106, Aug. 2009, pp. 12617-12622.

L. Malic, T. Veres, and M. Tabrizian, "Biochip functionalization using electrowetting-on-dielectric digital microfluidics for surface plasmon resonance imaging detection of DNA hybridization.," Biosensors & Bioelectronics, vol. 24, Mar. 2009, pp. 2218-2224.

G.J. Shah, A.T. Ohta, E.P.-Y. Chiou, M.C. Wu, and C.-J.C.J. Kim, "EWOD-driven droplet microfluidic device integrated with optoelectronic tweezers as an automated platform for cellular isolation and analysis.," Lab on a Chip, vol. 9, Jun. 2009, pp. 1732-1739.

Yang, C.-G., Z.-R. Xu, and J.-H. Wang, "Manipulation of droplets in microfluidic systems," Trends in Analytical Chemistry, vol. 29, Feb. 2010, pp. 141-157.

Malic, L., D. Brassard, T. Veres, and M. Tabrizian, "Integration and detection of biochemical assays in digital microfluidic LOC devices," Lab on a chip, vol. 10, Feb. 2010, pp. 418-431.

Y.-Jun Shin and J.-bong Lee, "Machine vision for digital microfluidics," Review of Scientific Instruments, vol. 81, 2010, p. 014302.

Fair, et al., "Integrated chemical/biochemical sample collection, preconcentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.

* cited by examiner

MODULAR DROPLET ACTUATOR DRIVE

1. RELATED APPLICATIONS

This application is a continuation of International Patent Application No. PCT/US2008/073673, entitled "Modular Droplet Actuator Drive," filed Aug. 20, 2008, which claims the benefit of, is related to, and incorporates by reference related provisional U.S. Patent Application Nos. 60/956,774, entitled "Modular Droplet Actuator Drive," filed on Aug. 20, 2007 and 60/980,503, entitled "Modular Droplet Actuator Drive," filed on Oct. 17, 2007.

This application is also a continuation-in-part of U.S. patent application Ser. No. 11/838,388, entitled "System for Controlling a Droplet Actuator," filed Aug. 14, 2007, pending, which is a continuation of International Patent Application No. PCT/US2007/011298, entitled "Droplet Manipulation Systems," filed May 9, 2007, which claims the benefit of, is related to, and incorporates by reference related provisional U.S. Patent Application Nos. 60/746,797, entitled "Portable Analyzer Using Droplet-Based Microfluidics," filed on May 9, 2006 and 60/806,412, entitled "Systems and Methods for Droplet Microactuator Operations," filed on Jun. 30, 2006.

2. GRANT INFORMATION

This invention was made with government support under NNJ06JD53C awarded by NASA. The government has certain rights in the invention.

3. BACKGROUND

Droplet actuators are used to conduct a wide variety of droplet operations. A droplet actuator typically includes two plates separated by a gap. The plates include electrodes for conducting droplet operations. The space is typically filled with a filler fluid that is immiscible with the fluid that is to be manipulated on the droplet actuator. The formation and movement of droplets is controlled by electrodes for conducting a variety of droplet operations, such as droplet transport and droplet dispensing. Because there are multiple types of assays that require multiple types of droplet actuator instrumentation, there is a need for flexible droplet actuator instruments that are capable of performing multiple types of assays.

4. BRIEF DESCRIPTION OF THE INVENTION

The invention provides a droplet actuator drive. In certain embodiments, the droplet actuator drive may include a detection apparatus for sensing a property of a droplet on a droplet actuator; circuitry for controlling the detection apparatus electronically coupled to the detection apparatus; a droplet actuator cartridge connector; circuitry for controlling a droplet actuator coupled to the droplet actuator connector; and/or a means for coupling the droplet actuator circuitry to a processor. The droplet actuator cartridge connector may be arranged so that when a droplet actuator cartridge is electronically coupled thereto, the droplet actuator cartridge is aligned with the detection apparatus; and the detection apparatus can sense the property of the droplet on a droplet actuator.

In some embodiments, the means for coupling the circuitry to a processor includes a set of connections for electrically coupling the circuitry to a computer, and/or means for wirelessly coupling the circuitry to a computer. The means for coupling the circuitry to a processor may include a droplet actuator drive configured for insertion in and electronic coupling to a computer via a drive bay of a desktop or laptop computer. For example, the droplet actuator drive may be configured as a desktop drive.

In some cases, the droplet actuator cartridge connector comprises a slide-out tray, and electronically coupling the droplet actuator cartridge connector to the processor is accomplished by (i) opening the slide-out tray; (ii) inserting the droplet actuator cartridge into the slide-out tray; and (iii) closing the slide-out tray.

The droplet actuator drive may be provided in a configuration suitable for insertion into a memory stick slot. The droplet actuator drive may be provided in a configuration suitable for insertion into a USB port. The means for coupling the droplet actuator circuitry to a processor comprises a male USB connector integrated with the droplet actuator drive.

The droplet actuator drive may include two or more of the droplet actuator cartridge connectors. The two or more droplet actuator cartridge connectors may include two or more connectors each configured for a different droplet actuator cartridge specific for a different droplet actuator test type.

In some cases, the droplet actuator drive may include an output mechanism for providing output indicative of sensing by the detection apparatus of a property of a droplet on the droplet actuator.

The droplet actuator drive may also include means for coupling the detector circuitry to a processor.

In some cases, the droplet actuator cartridge connector includes a slot configured for insertion of a droplet actuator cartridge.

In some cases, the detection apparatus comprises a sensor for sensing photons emitted from and/or transmitted through a droplet on the droplet actuator.

In some cases, a droplet actuator cartridge electronically coupled to the droplet actuator cartridge connector. The droplet actuator cartridge may include an optically transparent region which aligns with the detection apparatus, permitting sensing of a property of a droplet on a droplet actuator.

In some cases, the droplet actuator drive also includes reagents for a predetermined assay type pre-loaded on the droplet actuator cartridge and a sample loaded on the droplet actuator cartridge prior to insertion into the slot. For example, in some cases, the reagents include nucleic acid amplification reagents; immunoassay reagents; and/or biochemistry reagents.

The invention also provides a system including a droplet actuator drive and a processor coupled to the means for coupling the detector circuitry to a processor. The system may be programmed to control the droplet actuator and/or detection apparatus. The processor may be a component of a computer selected from the group consisting of desktop computers, laptop computers, and handheld computers. The system may also include a droplet actuator cartridge electronically coupled to the droplet actuator cartridge connector.

In other embodiment, the invention includes a kit. The kit may, for example, include packaged elements, such as a droplet actuator drive. The kit may include a droplet actuator drive along with one or more droplet actuators. The kit may include droplet actuators along with one or more reagents for loading on the droplet actuators. For example, the kit may include beads for conducting an assay using the droplet actuator cartridge. The beads may be provided pre-loaded on the droplet actuator cartridge.

The kit may include instructions for using the kit. The instructions may be electronically stored on an electronic storage medium associated with the cartridge such that when coupled to a droplet actuator drive, the instructions are displayed on an output device associated with the droplet actuator drive and or a system comprising the droplet actuator drive.

The invention also provides methods of conducting assays. For example, a method may involve providing a droplet actuator drive of the invention; electronically coupling the droplet actuator drive to a computer processor; coupling a droplet actuator cartridge to a droplet actuator cartridge connector, the cartridge comprising reagent sample for an assay protocol; executing software using the computer processor to effect droplet operations steps and other steps for conducting the assay. For example, the steps may include executing steps in the assay protocol; sensing a property of an assay droplet; and/or displaying an output indicative of the property of the assay droplet.

In some cases, the methods of the invention include conducting one or more droplet operations using droplets comprising one or more beads; conducting one or more droplet operations using droplets comprising one or more biological cells; conducting one or more dispensing or splitting droplet operations using droplets comprising beads; conducting one or more dispensing or splitting droplet operations using droplets comprising biological cells; conducting one or more dispensing or splitting droplet operations using droplets comprising viable biological cells; conducting one or more washing operations using magnetically responsive beads; conducting one or more washing operations using substantially non-magnetically responsive beads.

5. DEFINITIONS

As used herein, the following terms have the meanings indicated.

"Activate" with reference to one or more electrodes means effecting a change in the electrical state of the one or more electrodes which results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator; configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads are described in U.S. Patent Publication No. 2005-0260686, entitled, "Multiplex flow assays preferably with magnetic particles as solid phase," published on Nov. 24, 2005, the entire disclosure of which is incorporated herein by reference for its teaching concerning magnetically responsive materials and beads. It should also be noted that various droplet operations described herein which can be conducted using beads can also be conducted using biological cells.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, capillary loading, fingerstick loading (or in general loading from a source such as humans or animals (tail snips on mice)), and pipette loading. Droplet operations may be mediated by electrodes and/or electric fields, using a variety of techniques, such as, electrowetting and/or dielectrophoresis. In some cases, droplet operations are further facilitated by the use of hydrophilic and/or hydrophobic regions on surfaces and/or by physical obstacles.

"Washing" with respect to washing a magnetically responsive bead means reducing the amount of one or more substances in contact with the magnetically responsive bead or exposed to the magnetically responsive bead from a droplet in contact with the magnetically responsive bead. The reduction in the amount of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial total amount of a substance. The washing operation may proceed using a variety of droplet operations. The washing operation may yield a droplet including the magnetically responsive bead, where the droplet has a total amount of the substance which is less than the initial amount of the substance. Other embodiments use substantially non-magnetically responsive beads, and immobilization may be achieved using various physical barriers, e.g., as described in U.S. Patent Application No. 60/957,717, filed on Aug. 24, 2007, entitled "Bead manipulations in a droplet actuator," the entire disclosure of which is incorporated herein by reference.

The terms "top" and "bottom," when used, e.g., to refer to the top and bottom substrates of the droplet actuator, are used for convenience only; the droplet actuator is functional regardless of its position or orientation in space.

When a given component, such as a layer, region or substrate, is referred to herein as being disposed or formed "on" another component, that given component can be directly on the other component or, alternatively, intervening components (for example, one or more coatings, layers, interlayers, electrodes or contacts) can also be present. It will be further understood that the terms "disposed on" and "formed on" are used interchangeably to describe how a given component is positioned or situated in relation to another component. Hence, the terms "disposed on" and "formed on" are not intended to introduce any limitations relating to particular methods of material transport, deposition, or fabrication.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct droplet operations on the droplet, the droplet is arranged on the droplet actuator in a manner which facilitates sensing of a property of or a signal from the droplet, and/or the droplet has been subjected to a droplet operation on the droplet actuator, e.g., a layer of filler fluid.

7. DESCRIPTION

The invention provides modular drive configurations for handling multiple types of assays. In one embodiment, the invention provides a standalone, assay-specific, droplet operations drive that is suitable for use with a corresponding assay-specific droplet actuator cartridge. In another embodiment, the invention provides a host instrument that is suitable for use with multiple types of assay-specific droplet operations drives. In yet other embodiments, droplet operations drives are provided that have standard computer form factors, which allow easy installation in any standard drive bay of any standard desktop or laptop computer or a handheld computer. The modular drive configurations provide flexible reuse of instruments, user configurability, and scalability.

7.1 Standalone Droplet Operations Drive

Figure 1:
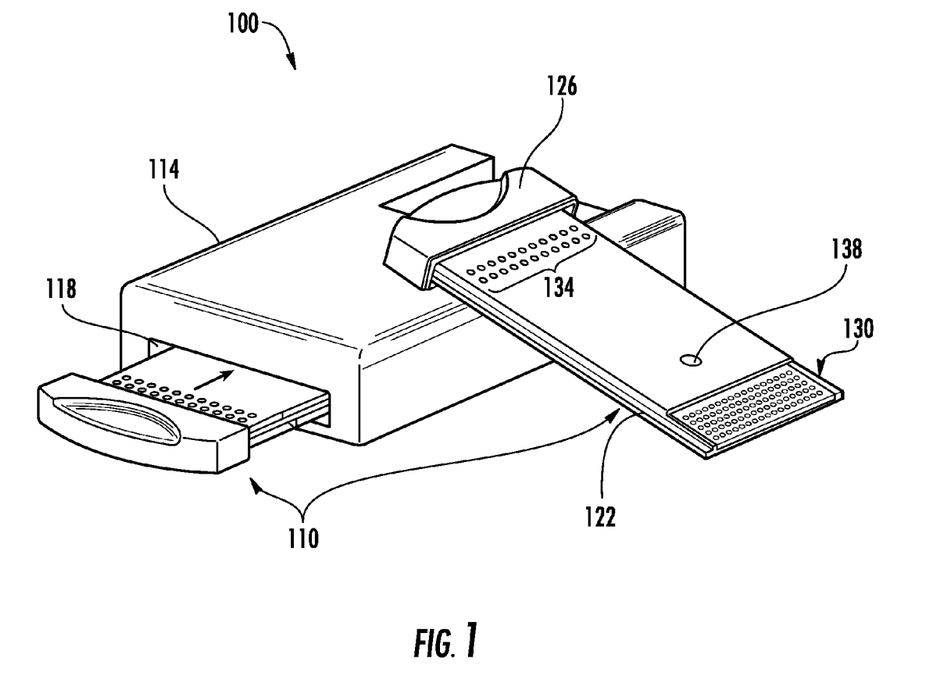
FIG. 1 illustrates a perspective view of a non-limiting example of a standalone droplet operations drive according to the present invention.

FIG. 1 illustrates a perspective view of a non-limiting example of a standalone droplet operations drive 100. The drive may include specific detection and sensing apparatus, and may, thus, be suitable for a specific subset of assay types. The drive is configured for use with a certain corresponding assay-specific droplet actuator cartridge 110, which includes a corresponding assay-specific droplet actuator (not shown) that is installed therein and electronics for coupling the droplet actuator to the drive. In one example, droplet operations drive 100 and a corresponding droplet actuator cartridge 110 are designed for performing immunoassays and, thus, the invention provides an immunoassay-specific droplet operations drive 100 and an immunoassay-specific droplet actuator cartridge 110. In another example, droplet operations drive 100 and a corresponding droplet actuator cartridge 110 are designed for performing polymerase chain reaction (PCR) assays and, thus, the invention provides a PCR-specific droplet operations drive 100 and a PCR-specific droplet actuator cartridge 110. In yet another example, droplet operations drive 100 and droplet actuator cartridge 110 are designed for performing biochemistry assays including DNA sequencing and, thus, the invention provides a biochemistry assay-specific droplet operations drive 100 and a biochemistry assay-specific droplet actuator cartridge 110.

Droplet operations drive 100 may include a body 114 for housing control circuitry (not shown) and detection mechanisms (not shown) that may be common to multiple assay-specific droplet actuator cartridges 110. For example, a PCR-specific droplet operations drive 100 houses PCR-specific control circuitry and PCR-specific detection mechanisms that may be used in common to multiple designs of PCR-specific droplet actuator cartridges 110.

Body 114 of droplet operations drive 100 may, for example, be formed of any suitably rigid and lightweight material, such as molded plastic or metal. Droplet operations drive 100 may be provided in a form factor that is suitably small to fit in a handheld device. In one example, body 114 is about 5 inches long, about 3 inches wide, and about 1 inch high so that it can fit into any standard multiwell plate reader for detection. In another example, the body may be in the form of a USB thumb drive or an SD card so that the cartridge can be directly inserted into a port on a computer. Additionally, certain analysis software (not shown) that drives the multiple types of droplet actuator cartridges 110 may be loaded on the hardware within droplet operations drive 100 and/or on an associated computer system that controls droplet operations drive 100.

Droplet actuator cartridge 110 may be installed in a slot 118 at one end of body 114. A set of power and signal I/O connectors (not shown) may be provided at the opposite end of body 114. A corresponding set of electrical connections (not shown) are provided inside the cavity formed by slot 118 of droplet operations drive 100 for connecting to the certain droplet actuator cartridge 110 that is installed therein. The cartridge may also contain magnets or electromagnets to enable magnetic operations and heaters & coolers to enable thermal operations.

Because droplet actuator cartridge 110 may be assay-specific, droplet actuator cartridge 110 may include an assay-specific droplet actuator (not shown) within a body 122. In one example, droplet actuator cartridge 110 is designed for performing immunoassays and, therefore, includes an immunoassay droplet actuator. In another example, a certain droplet actuator cartridge 110 is designed for performing DNA amplification assays and, therefore, includes a DNA amplification droplet actuator. In yet another example, droplet actuator cartridge 110 is designed for performing biochemistry assays and, therefore, includes a biochemistry assay droplet actuator, and may also include reagents. In yet another example, assay-specific reagents may be loaded on the droplet actuator and/or droplet actuator cartridge 110. In another embodiment, a combination cartridge is designed to perform a combination of biochemistry assays such as DNA amplification and immunoassays, DNA amplification and DNA sequencing and other combinations of biochemical assay types.

Body 122 of droplet actuator cartridge 110 may, for example, be formed of any suitably rigid and lightweight material, such as molded plastic or metal. Alternatively, body 122 of droplet actuator cartridge 110 may, for example, be formed of a heavy duty material that is suitable for field or military use. A grip 126 may be incorporated at one end of body 122 for easy handling of droplet actuator cartridge 110. Body 122 may also include a set of electrical connections 130, such as a set of conductive pads, for providing power is signal I/O to the droplet actuator arranged so that when the cartridge is installed, the contacts are electrically coupled with corresponding connections associated with the drive. Additionally, droplet actuator cartridge 110 may include a sample/reagent input 134, which is fluidly connected to the droplet actuator. In one example, sample/reagent input 134 includes openings that allow for easy pipetting of samples or reagents. In another example, the sample liquid may be directly "sipped" into the cartridge by capillary flow for further analysis. In this example, the openings may be sealable by an array of caps or by tape. Furthermore, droplet actuator cartridge 110 includes a detection area 138. Droplet actuator cartridge 110 may include detection area 138, which is arranged is such that it automatically aligns with a detector (not shown) within body 114 of droplet operations drive 100 when droplet actuator cartridge 110 is installed therein.

The design of slot 118 of droplet operations drive 100 in combination with the design of droplet actuator cartridge 110 may include a push-actuated connection. More specifically, droplet actuator cartridge 110 and slot 118 of droplet operations drive 100 may be designed so that pushing droplet actuator cartridge 110 into slot 118 locks droplet actuator cartridge 110 in place and makes the electrical contacts.

By way of example, the use of droplet operations drive 100 in a DNA amplification assay application may be summarized as follows. A user electrically couples a certain DNA amplification-specific droplet operations drive 100 to a user interface device, such as a desktop or laptop computer; the user then selects a first type of assay-specific droplet actuator cartridge 110; loads a sample in the cartridge; inserts the first DNA amplification-specific droplet actuator cartridge 110 into slot 118 of the DNA amplification-specific droplet operations drive 100; executes the assay-specific protocol; and receives a first set of assay-specific assay results. Subsequently, the user removes the first assay-specific droplet actuator cartridge 110 from the assay-specific droplet operations drive 100; inserts a second type of assay-specific droplet actuator cartridge 110 into slot 118 of the DNA amplification-specific droplet operations drive 100; executes the assay-specific protocol; and receives a second set of assay-specific assay results. The above process may be repeated for a third, fourth, fifth, and so on, type of DNA amplification-specific droplet actuator cartridge 110. Alternatively, multiple assays and droplet operations drives may be operated in parallel, which is described further in the next section.

7.2 Host Instrument for Multiple Droplet Operations Drives

Figure 2:
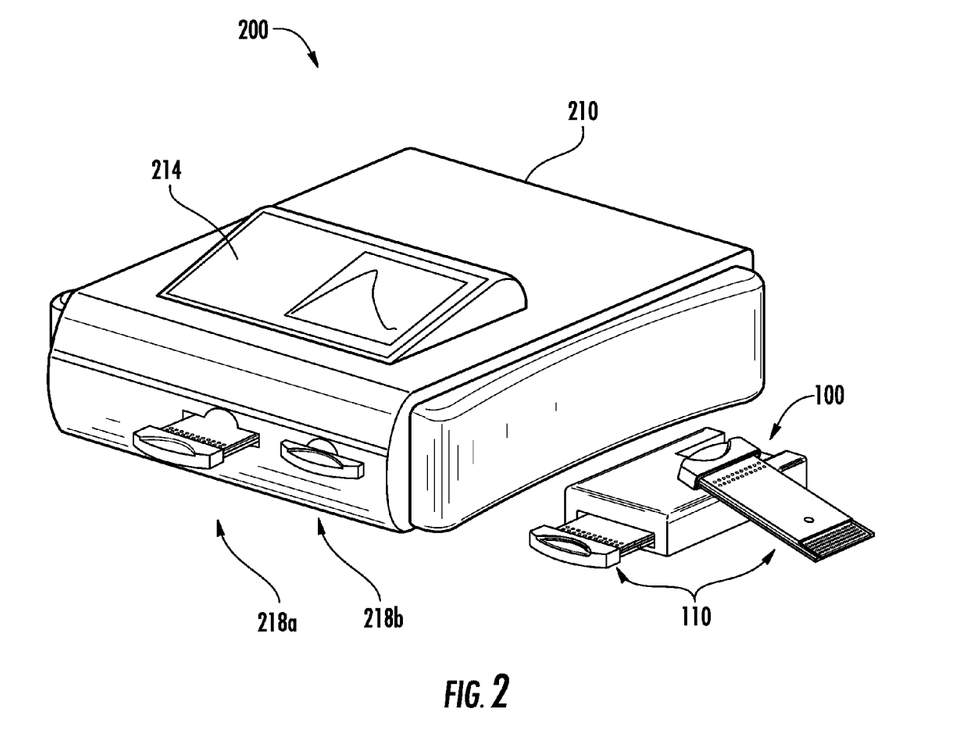
FIG. 2 illustrates a perspective view of a non-limiting example of a host instrument according to the present invention, which provides a modular standalone configuration of droplet operations drives, which is suitable for use as, for example, a benchtop analyzer device.

FIG. 2 illustrates a perspective view of a non-limiting example of a host instrument 200, which provides a modular standalone configuration of droplet operations drives 100, which is suitable for use as, for example, a benchtop analyzer device. A body 210 of host instrument 200 may house a controller unit (not shown), which may include compact electronics for droplet control, and a detection unit (not shown), which may, for example, include a photomultiplier tube (PMT) for chemiluminescence detection, LED/APD for fluorescence detection, optional modular detection units that are available via fiber coupling, and any combinations thereof. Alternatively, the detection unit can include electrical connections for electrical readout of signals produced by droplets (electrochemical, amperometric, potentiometric, conductometric, impedance-based etc). The detection unit can also include means for detecting magnetism. The controller unit and detection unit may provide functionality for multiple types of assays, such as, but not limited to, immunoassays, DNA amplification assays, and biochemistry assays. Additionally, analysis software may be loaded on the hardware of host instrument 200 that is suitable of performing the multiple types of assays. A user interface 214, such as a touch screen, is provided for operating host instrument 200.

Additionally, host instrument 200 includes one or more drive bays 218 (e.g., drive bays 218a and 218b). In one embodiment, drive bays 218 allow for swapping drives in any combination. In other embodiments, drive bays 218 may be specific to certain types of droplet actuator cartridges. For example, within drive bays 218 of host instrument 200 may be installed one or more immunoassay-specific droplet operations drives 100, one or more DNA amplification-specific droplet operations drives 100, one or more biochemistry assay-specific droplet operations drives 100, and any combinations thereof.

Body 210 of host instrument 200 may, for example, be formed of any suitably rigid and lightweight material, such as molded plastic or metal. Alternatively, body 210 of host instrument 200 may, for example, be formed of a heavy duty material that is suitable for field or military use. In one example, body 210 of host instrument 200 is about 12 inches long, about 12 inches wide, and about 3.5 inches high.

By way of example, a user may install an assay-specific droplet operations drive 100, which has a corresponding assay-specific droplet actuator cartridge 110 inserted therein, in drive bay 218a and execute an assay-specific analysis thereon. At the same time, a user may install an assay-specific droplet operations drive 100, which has a corresponding assay-specific droplet actuator cartridge 110 inserted therein, in drive bay 218b and execute an assay-specific analysis thereon. Host instrument 200 may operate in a standalone mode. Alternatively, host instrument 200 may be connected to an external computing device, such as described in FIG. 3. The host instrument may also be a stack or a tower which incorporates multiple cartridges in a rack which is accessible for processing (such as fluid input and output) by robotics that are utilized in a high throughput environment.

Figure 3:
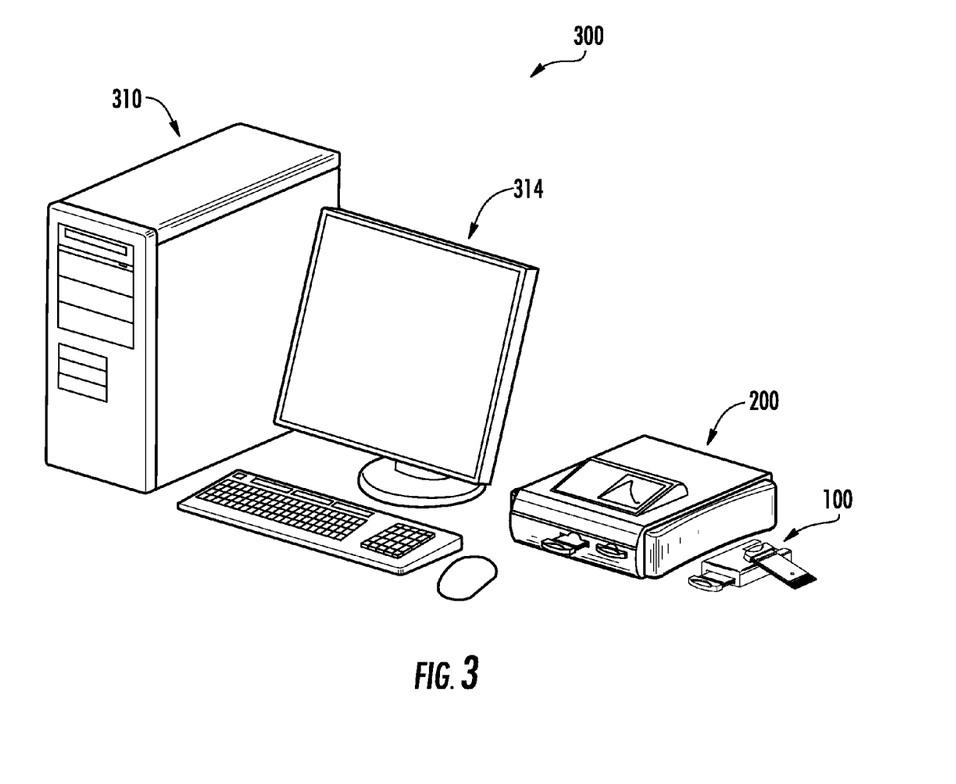
FIG. 3 illustrates a perspective view of a non-limiting example of a system according to the present invention that includes a computing device, such as a standard desktop or laptop computer, along with its associated user interfaces, such as a display, keyboard, and mouse.

FIG. 3 illustrates a perspective view of a non-limiting example of a system 300 that includes a computing device 310, such as a standard desktop or laptop computer, along with its associated user interfaces 314, such as a display, keyboard, and mouse. Additionally, system 300 includes at least one host instrument 200 of FIG. 2 that has a wired (e.g., USB or Firewire connection) or wireless (e.g., Bluetooth™ or IEEE 802.11 technology) communication link to computing device 310. In one example, the analysis software that drives the one or more droplet actuator cartridges 110, which are installed in the respective droplet operations drives 100 of host instrument 200, resides on computing device 310.

7.3 Droplet Operations Drives Having Standard Form Factors

Figure 4:
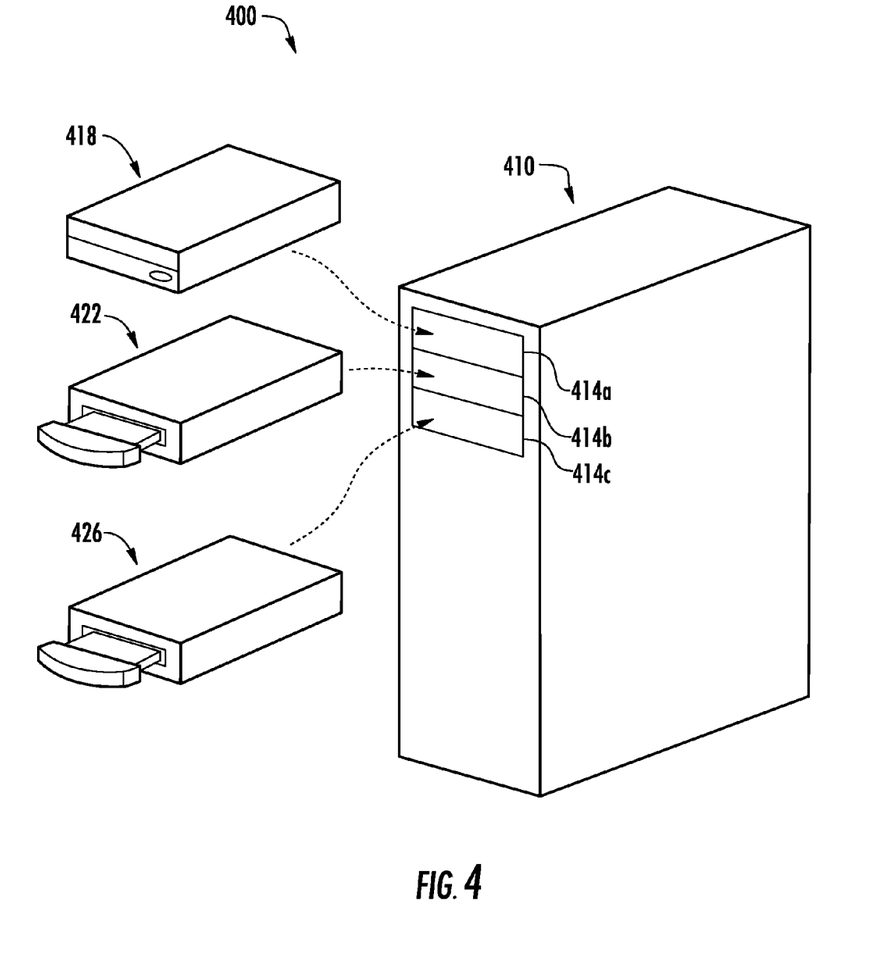
FIG. 4 illustrates a perspective view of a non-limiting example of a droplet operations drive configuration according to the present invention, which is a non-limiting example of a desktop computer-specific configuration.

FIG. 4 illustrates a perspective view of a non-limiting example of a droplet operations drive configuration 400, which is a non-limiting example of a desktop computer-specific configuration. More specifically, FIG. 4 shows a standard desktop computer 410 that includes standard 5.25 inch-drive bays 414, such as drive bays 414*a*, 414*b*, and 414*c*. In one example, a standard 5.25 inch-CD-ROM drive 418 is installed in drive bay 414*a*, a droplet operations drive 422 is installed in drive bay 414*b*, and a droplet operations drive 426 is installed in drive bay 414*c*. Droplet operations drives 422 and 426 are substantially the same as droplet operations drive 100 of FIG. 1, except that the bodies thereof have the same 5.25 inch-form factor as the standard 5.25 inch-drive bays 414. Droplet operations drives 422 and 426 include standard desktop computer power and signal connectors. In this way, a droplet operations drive may be installed in any standard desktop computer. More specifically, a user is provided one or more droplet operations drives and associated analysis software, which may be installed in the user's existing desktop computer.

Droplet operations drive configuration 400 is not limited to the configuration shown in FIG. 1. FIG. 1 is exemplary only. Droplet operations drive configuration 400 may include any number and combination of droplet operations drives and standard desktop computer drives (e.g., CD-ROM drive, floppy drive, etc).

Figure 5:
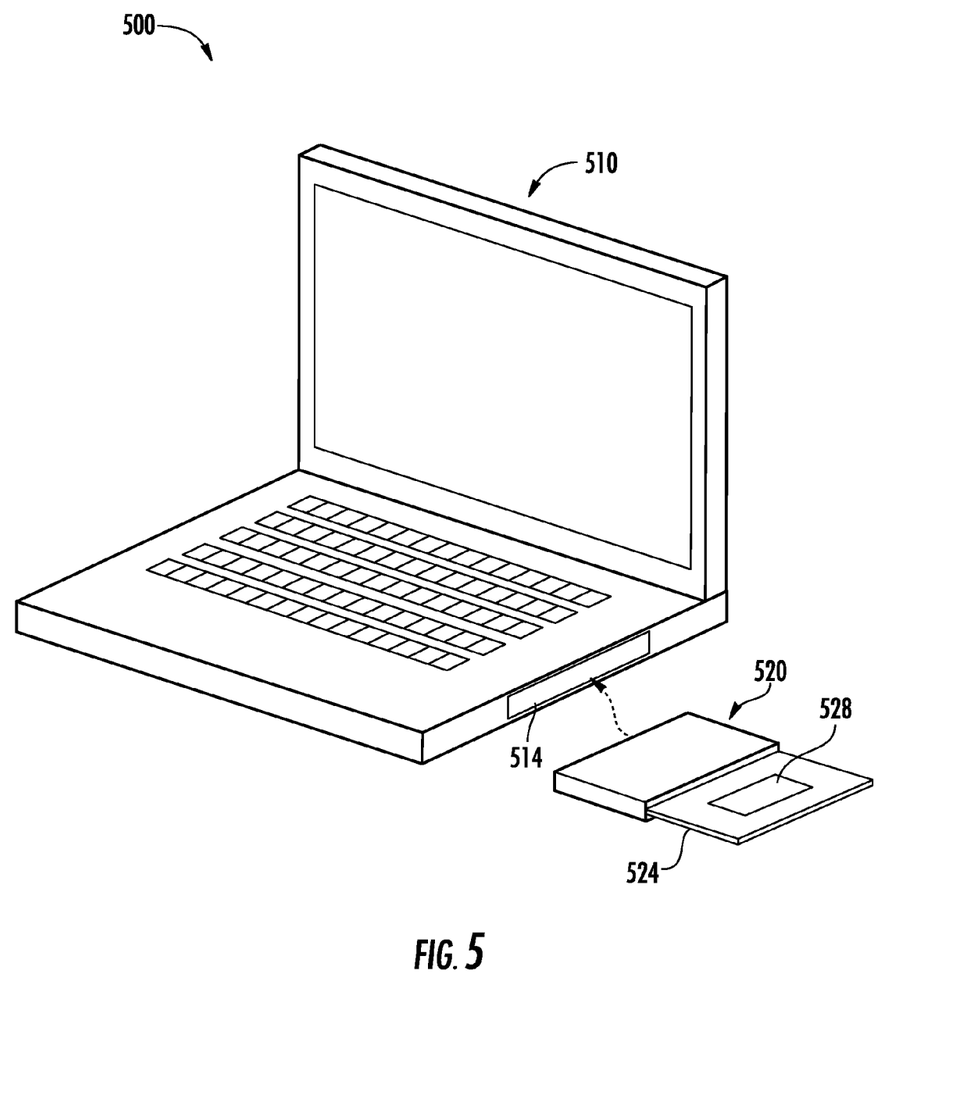
FIG. 5 illustrates a perspective view of a non-limiting example of a droplet operations drive configuration according to the present invention, which is a non-limiting example of a laptop computer-specific configuration.

FIG. 5 illustrates a perspective view of a non-limiting example of a droplet operations drive configuration 500, which is a non-limiting example of a laptop computer-specific configuration. More specifically, FIG. 5 shows a standard laptop computer 510 that includes standard laptop computer drive bay 514, such as a standard laptop computer CD-ROM or floppy drive bay. In one example, a droplet operations drive 520 is installed in drive bay 514. Droplet operations drive 520 is substantially the same as droplet operations drive 100 of FIG. 1, except that the body thereof has the same form factor as standard laptop computer drive bay 514. Droplet operations drive 520 includes standard laptop computer power and signal connectors. In this way, droplet operations drive 520 may be installed in any standard laptop computer. More specifically, a user is provided a droplet operations drive 520 and associated analysis software, which may be installed in his/her existing laptop computer.

Droplet operations drive 520 may include, for example, a standard slot for inserting a droplet actuator cartridge 110, such as described in droplet operations drive 100 of FIG. 1. Alternatively, and referring again to FIG. 5, droplet operations drive 520 may include a tray 524, which is similar to a standard CD-ROM tray, having a receptacle integrated therein for accepting a droplet actuator 528.

Alternatively, a droplet operations drive is designed to plug into the personal computer memory card international association (PCMCIA) card slot (not shown) of a standard laptop computer or an SD card or flash memory reader slot such as a USB slot.

Alternatively and referring again to FIGS. 4 and 5, the droplet operations drives may be provided as external drives (not shown) that may be connected to any standard computer (e.g., any standard desktop or laptop computer) in a wired fashion (e.g., USB connection, FireWire connection, or a parallel port or serial port connection; in this case the drive will include a separate power supply) or in a wireless fashion (e.g., Bluetooth™ or IEEE 802.11 technology).

Alternatively and referring again to FIGS. 4 and 5, a droplet operations drive may be integrated in a handheld computing device, into which a droplet actuator cartridge may be inserted. A droplet operations drive may also be interfaced with the secure-digital (SD) card slot on a handheld smartphone or a personal digital assistant or any mobile phone which can use the data communication capabilities of the mobile phone to communicate with a physician or a laboratory information system (LIS) or hospital information system (HIS).

Additionally, droplet operations drives, such as droplet operations drives 422 and 426 of FIG. 4 and droplet operations drive 520 of FIG. 5, which have standard drive bay form factors, may be easily installed in existing networked computers and used with existing standard communications protocols, in order to facilitate any number of applications. In one example, droplet operations drives may be installed in an existing network for enabling a bio-threat monitoring application. Alternatively, a portable bio-threat detection system may be formed by installing a droplet operations drives in any laptop computer.

7.4 Droplet Actuator and Sensors

For examples of droplet actuator architectures that are suitable for use with the present invention, see U.S. Pat. No. 6,911,132, entitled, "Apparatus for Manipulating Droplets by Electrowetting-Based Techniques," issued on Jun. 28, 2005 to Pamula et al.; U.S. patent application Ser. No. 11/343,284, entitled, "Apparatuses and Methods for Manipulating Droplets on a Printed Circuit Board," filed on filed on Jan. 30, 2006; U.S. Pat. Nos. 6,773,566, entitled, "Electrostatic Actuators for Microfluidics and Methods for Using Same," issued on Aug. 10, 2004 and 6,565,727, entitled, "Actuators for Microfluidics Without Moving Parts," issued on Jan. 24, 2000, both to Shenderov et al.; Pollack et al., International Patent Application No. PCT/US 06/47486, entitled, "Droplet-Based Biochemistry," filed on Dec. 11, 2006, the disclosures of which are incorporated herein by reference. International Patent Application No. PCT/US 07/09379, entitled "Droplet Manipulation Systems," describes user interfaces, cartridge and droplet actuator electronics that are suitable for use in the present invention, the entire disclosure of which is incorporated herein by reference.

7.5 Method of Using a Standalone Droplet Operations Drive

A method of using a standalone, assay-specific, droplet operations drive includes, but is not limited to, one or more of the following steps. (1) electrically coupling a certain assay-specific droplet operations drive to a user interface device, such as a desktop or laptop computer; (2) selecting a certain assay-specific (includes multiple specific assays or assay types) droplet actuator cartridge; (3) inserting the certain assay-specific droplet actuator cartridge into the slot of the assay-specific droplet operations drive; (4) executing the assay-specific analysis software; (5) receiving a certain set of assay-specific assay results; (6) removing the certain assay-specific droplet actuator cartridge from the assay-specific droplet operations drive; (7) inserting a next type of assay-specific droplet actuator cartridge into slot of the assay-specific droplet operations drive; (8) executing the assay-specific analysis software; (9) receiving a next set of assay-specific assay results; and (10) repeating steps 6 through 9 for any number of assay-specific droplet actuator cartridges.

8. CONCLUDING REMARKS

The foregoing detailed description of embodiments refers to the accompanying drawings, which illustrate specific embodiments of the invention. Other embodiments having different structures and operations do not depart from the scope of the present invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

We claim:

1. A kit comprising:
   a. a droplet actuator cartridge comprising:
      i. a droplet actuator; and
      ii. means for coupling the droplet actuator cartridge to a droplet actuator drive; and
   b. beads for conducting an assay using the droplet actuator cartridge; and
   c. instructions for using the droplet actuator cartridge.

2. The kit of claim 1 wherein the beads are loaded on the droplet actuator cartridge.

3. The kit of claim 2 further comprising instructions for using the kit.

4. The kit of claim 3 wherein the instructions are electronically stored on an electronic storage medium associated with the cartridge such that when coupled to a droplet actuator drive, the instructions are displayed on an output device associated with the droplet actuator drive and or a system comprising the droplet actuator drive.

5. A method of conducting an assay, the method comprising:
   a. providing a droplet actuator drive comprising:
      i. a detection apparatus for sensing a property of a droplet on a droplet actuator;
      ii. circuitry for controlling the detection apparatus electronically coupled to the detection apparatus;
      iii. a droplet actuator cartridge connector arranged so that when a droplet actuator cartridge electronically coupled thereto:
         1. the droplet actuator cartridge is aligned with the detection apparatus; and
         2. the detection apparatus can sense the property of the droplet on a droplet actuator;
      iv. circuitry for controlling a droplet actuator coupled to the droplet actuator connector;
      v. means for coupling the droplet actuator circuitry to a processor; and
   b. electronically coupling the droplet actuator drive to a computer processor;
   c. coupling a droplet actuator cartridge to a droplet actuator cartridge connector, the cartridge comprising reagent sample for an assay protocol;
   d. executing software using the computer processor to effect steps comprising:
      i. executing steps in the assay protocol, the steps comprising conducting one or more dispensing or splitting droplet operations using droplets comprising beads;
      ii. sensing a property of an assay droplet; and
      iii. displaying an output indicative of the property of the assay droplet.

6. The method of claim 5 wherein step 5.d.i comprises conducting one or more droplet operations using droplets comprising one or more beads.

7. The method of claim 5 wherein step 5.d.i comprises conducting one or more droplet operations using droplets comprising one or more biological cells.

8. The method of claim 5 wherein step 5.d.i comprises conducting one or more dispensing or splitting droplet operations using droplets comprising biological cells.

9. The method of claim 5 wherein step 5.d.i comprises conducting one or more dispensing or splitting droplet operations using droplets comprising viable biological cells.

10. The method of claim 5 wherein step 5.d.i comprises conducting one or more washing operations using magnetically responsive beads.

11. The method of claim 5 wherein step 5.d.i comprises conducting one or more washing operations using substantially non-magnetically responsive beads.

12. The method of claim 5 wherein the property of the assay droplet sensed in step 5.d.ii is indicative of a property of one or more beads in the assay droplet.

13. The method of claim 5 wherein the property of the assay droplet sensed in step 5.d.ii is indicative of a property of one or more biological cells in the assay droplet.

14. The method of claim 5 wherein the output displayed in step 5.d.iii is indicative of a property of one or more beads in the assay droplet.

15. The method of claim 5 wherein the output displayed in step 5.d.iii is indicative of a property of one or more cells in the assay droplet.

* * * * *

UNITED STATES PATENT AND TRADEMARK OFFICE
CERTIFICATE OF CORRECTION

PATENT NO. : 8,041,463 B2  
APPLICATION NO. : 12/707081  
DATED : October 18, 2011  
INVENTOR(S) : Michael G. Pollack et al.

Page 1 of 1

It is certified that error appears in the above-identified patent and that said Letters Patent is hereby corrected as shown below:

Title Page, Item (57) should read
Inventors: Michael G. Pollack, Durham, NC (US); Vamsee K. Pamula, Durham, NC (IN), Vijay Srinivasan, Durham, NC (IN), Allen E. Eckhardt, Durham, NC (US), Richard B. Fair, Durham, NC (US), and Philip Y. Paik, Chula Vista, CA (US).

Signed and Sealed this
Fourteenth Day of February, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,041,463 B2 | Page 1 of 1 |
| APPLICATION NO. | : 12/707081 | |
| DATED | : October 18, 2011 | |
| INVENTOR(S) | : Michael G. Pollack et al. | |

It is certified that error appears in the above-identified patent and that said Letters Patent is hereby corrected as shown below:

Title Page, Item (75) should read
Inventors: Michael G. Pollack, Durham, NC (US); Vamsee K. Pamula, Durham, NC (IN), Vijay Srinivasan, Durham, NC (IN), Allen E. Eckhardt, Durham, NC (US), Richard B. Fair, Durham, NC (US), and Philip Y. Paik, Chula Vista, CA (US).

This certificate supersedes the Certificate of Correction issued February 14, 2012.

Signed and Sealed this
Twentieth Day of March, 2012

David J. Kappos
*Director of the United States Patent and Trademark Office*